United States Patent
Haley

(10) Patent No.: US 7,201,930 B2
(45) Date of Patent: Apr. 10, 2007

(54) LICORICE ROOT EXTRACT ORAL PATCH FOR TREATING CANKER SORES

(76) Inventor: Jeffrey T. Haley, 4730-91st Ave. SE., Mercer Island, WA (US) 98040

( * ) Notice: Subject to any disclaimer, the term of this patent is extended or adjusted under 35 U.S.C. 154(b) by 275 days.

(21) Appl. No.: 10/772,099

(22) Filed: Feb. 4, 2004

(65) Prior Publication Data

US 2004/0156930 A1    Aug. 12, 2004

Related U.S. Application Data

(63) Continuation-in-part of application No. PCT/US02/35399, filed on Nov. 5, 2002.

(60) Provisional application No. 60/344,577, filed on Dec. 28, 2001, provisional application No. 60/332,916, filed on Nov. 5, 2001.

(51) Int. Cl.
    *A61K 36/236*    (2006.01)
(52) U.S. Cl. .................. 424/757; 424/725
(58) Field of Classification Search ........... 424/725, 424/757
    See application file for complete search history.

(56) References Cited

U.S. PATENT DOCUMENTS

| | | |
|---|---|---|
| 5,198,217 A * | 3/1993 | Vedros ............... 424/757 |
| 5,362,737 A | 11/1994 | Vora et al. |
| 5,409,703 A | 4/1995 | McAnalley et al. |
| 5,700,478 A * | 12/1997 | Biegajski et al. ........ 424/434 |
| 5,713,852 A | 2/1998 | Anthony et al. |
| 5,800,832 A | 9/1998 | Tapolsky et al. |
| 6,159,498 A | 12/2000 | Tapolsky et al. |
| 6,197,331 B1 | 3/2001 | Lerner et al. |
| 6,248,718 B1 | 6/2001 | Hau |
| 6,555,125 B2 | 4/2003 | Campbell |
| 6,585,997 B2 | 7/2003 | Moro et al. |
| 2003/0003140 A1 | 1/2003 | Domb et al. |
| 2005/0263985 A1 | 12/2005 | Miller |

FOREIGN PATENT DOCUMENTS

WO    WO 03/039465 A3    5/2003

* cited by examiner

*Primary Examiner*—Patricia Leith
(74) *Attorney, Agent, or Firm*—Graybeal Jackson Haley LLP

(57) ABSTRACT

A method for treating mouth ulcers (canker sores/aphthous ulcers) with licorice extract oral patches to speed healing and relieve pain. If licorice extract is applied to a mouth ulcer using an adhesive oral patch that delivers the medication for at least 30 minutes and the patches are used for at least two or more hours per day, the method reduces the healing times from typically 10–14 days to typically 2 days. The licorice extract patches also quickly reduces canker sore pain and, if used before commencing a meal, reduces pain during the meal. A fully dissolving patch with licorice extract and collagen is disclosed.

10 Claims, 1 Drawing Sheet

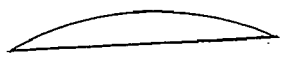
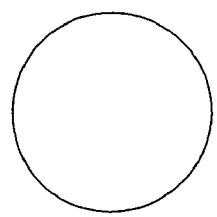
Fig. 1a    Fig. 1b
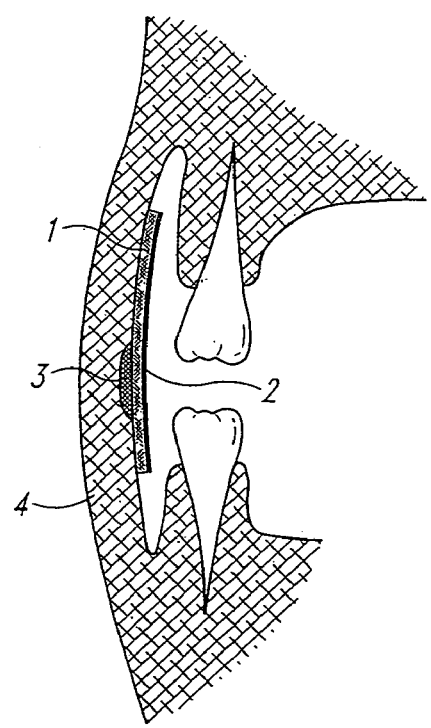
Fig. 2

LICORICE ROOT EXTRACT ORAL PATCH FOR TREATING CANKER SORES

This application is a CIP of PCT/US02/35399 filed Nov. 5, 2002 which claims benefit of priority to provisional application US 60/332,916 filed Nov. 5, 2001 and to provisional application US 60/344,577 filed Dec. 28, 2001.

BACKGROUND

To deliver a medication in the mouth over time for treatment of health problems in the mouth or throat, oral patches have been developed. An oral patch typically includes one or more flexible layers that do not dissolve entirely such as invented by Anthony et al. and disclosed in U.S. Pat. No. 5,713,852. Another example of an oral patch is the DentiPatch which has one or more non-soluble thermo-plastic layers and lidocaine, offered for sale by Noven Pharmaceuticals, Inc.

As used herein, the word "patch" does not include preparations that move about the mouth rather than adhering in one place, such as cough drops or throat lozenges, and therefore do not maintain a high concentration of released medication in the desired spot. Nor does it include preparations that do not hold together as a single item when held in the mouth such as preparations of powder, liquid, paste, viscous liquid gel, or a tablet or troche that crumbles into a powder or paste when chewed or placed in saliva. Conversely, it does include an adherent preparation formed of a gelled hydrocolloid that holds together as a single item when held in the mouth, such as the adherent, soluble oral patch disclosed by the same inventor in U.S. patent application Ser. No. 10/287,843 filed Nov. 5, 2002, which is incorporated herein by this reference.

The most significant differences between an oral patch as used herein and other forms of medicinal preparations is that an oral patch is designed to release medication into the mouth over a relatively long period of time, such as 30 minutes of more, and be adherent to stay in one place so that the medication can reach high concentrations along side the patch, and remain in the mouth as a single item that will not spread to be in a plurality of location in the mouth at one time.

It has been known for many decades that licorice root (*Glycyrrhiza*) includes an ingredient that speeds the healing of ulcers in the stomach. It is not yet known which ingredient in licorice root is responsible. More recently it has been discovered that a majority of stomach ulcers are caused by bacteria called *Helicobacter pylori* and that most stomach ulcers are therefore treatable with pharmaceutical antibiotics. This suggests that the active ingredient in licorice root is an antimicrobial that interferes with the *Helicobacter pylori* bacteria or with a reaction of stomach tissues to the bacteria.

For treatment of ulcers in the stomach, powdered licorice root extract is sometimes swallowed in gelatin capsules. However, it is believed that the extract is more effective if it is mixed with saliva before being swallowed. Therefore, chewable licorice extract tablets and lozenges have been developed. The extract powder is compressed into a tablet or lozenge form that quickly crushes into a mass of powder or paste when chewed. Even if it is not chewed, when exposed to saliva, it quickly dissolves into a mass of past and mixes with saliva. All of these licorice extract tablets and lozenges are designed to be chewed and the resulting paste swallowed. It is not known to put licorice extract in an oral adhesive patch.

Physicians in India have determined with clinical trials that licorice extract is also effective for speeding the healing of ordinary mouth ulcers, commonly called canker sores, technically called aphthous ulcers, when the extract mixed with water is swished in the mouth several times per day. Das S K, Gulati A K, Singh V P; De-glycyrrhizinated Licorice in Aphthous Ulcers; *J Assoc Physicians India*, 1989, 37:647. It also quickly relieves pain from canker sores without numbing surrounding tissues.

Other physicians (Andrew Weil) have reported success in speeding the healing of canker sores using propolis, made by bees, which is believed to have antimicrobial effects.

As reported in standard medical references, topical application of pharmaceutical antibiotics such as tetracycline or penicillin have been shown to speed healing of canker sores (aphthous ulcers) when swished as a liquid in the mouth several times per day. Alternatively, antibiotics may be applied to the canker sore several times per day as a powder, paste, or viscous liquid gel or they may be placed into the mouth as a tablt or troche which quickly dissolves into a liquid or paste, as disclosed by Hau in U.S. Pat. No. 6,248,718, the contents of which are incorporated herein by this reference. In addition to tetracycline and penicillin, other antibiotics such as amoxicillin have been shown effective when applied topically in a similar manner. Other products that have been reported to speed healing of canker sores when applied topically include anti-bacterials such as hydrogen peroxide, carbamide peroxide, chlorhexidine gluconate and, in at least one study, the antihistamine diphenhydramine.

Anti-inflammatory drugs, such as corticosteroids, reduce severity of canker sores but do not speed healing.

SUMMARY OF THE INVENTION

Through trials, the inventor has discovered that, when using licorice root (*glycyrrhiza*) extract for treatment of ordinary mouth ulcers (also called denture sores, canker sores or aphthous ulcers), it is better to keep the medication in the mouth or near the sore as many hours per day as possible through the use of an adhesive oral patch. Using a patch to keep the medication topically applied on or near the canker sore for about half of the hours in a day over 2 days, instead of merely applying a troche, gel, paste, or liquid six times per day for 2 days, transforms the results from nearly always ineffective to nearly always effective. With prompt and consistent use on each canker sore, the duration of each canker sore is reduced from typically 10–14 days without treatment to 1–3 days, typically 2 days, with licorice extract in a patch applied for half of the hours, day and night. For small or emergent canker sores, application for as little as two hours per day can be effective.

It may be that a relatively minor disruption or modification of microbial colonies within the ulcer, without significantly disrupting the same microbes elsewhere in the mouth, is sufficient to allow the ulcer to heal. The inventor has discovered that this disruption must be maintained over a substantial portion of each day through the use of an adhesive patch that releases medication over time to achieve high rates of effectiveness.

The inventor also discovered that when extract of licorice root is held on a canker sore with an oral patch for longer than 15 minutes, the canker sore pain is significantly reduced and there is no numbing of surrounding tissues. The pain relief continues while eating long enough to complete a meal with reduced pain.

In one aspect, the invention is a method for treating canker sores by providing patches which, when exposed to saliva in a human mouth, release extract of licorice root over more than 30 minutes and instructing people to hold the patches in their mouths on or near the canker sore for at least 2 or more hours per day. The extract of licorice root (*glycyrrhiza*) may be a water extract. Propolis or an extract of propolis may be substituted for licorice root extract. The patch may include a binder ingredient to hold and release the medication. The binder ingredient may be a gum that dissolves in saliva such as xanthan gum, konjac gum, gelatin, or locust bean gum.

In another aspect, the invention is a method for treating canker sores to relieve pain of canker sores without numbing surrounding tissues by providing a patch which, when exposed to saliva in the human mouth, releases extract of licorice root over more than 30 minutes and instructing recipients of the patches to use them on or near canker sores to relieve pain. The extract may have less glycyrrhizin (or its component glycyrrhizic acid) than a simple water extract. The patch may include a binder ingredient that dissolves in saliva, such as xanthan gum, konjac gum, gelatin, or locust bean gum.

In another aspect, the invention is an adherent oral patch that, when held in a human mouth, remains in the mouth as a single item that will not spread to be in a plurality of locations in the mouth at one time, lasts for more than 30 minutes, and releases high enough levels of extract of licorice root as well as collagen to be effective over time. Collagen, such as in the form of food grade gelatin, forms a coating on the ulcer that is soothing and acts as an adhesive if held in the patch with a binder that retains the long collagen molecules. The trick is to use binder materials that have the right dissolution (erosion) characteristics while comprising a minimum of the dry ingredients. By selecting the right binders and ratios of the ingredients, the release of licorice root extract will last more than 30 minutes, yet there will not be so much binding that the collagen provides insufficient adhesion and adequate amounts of licorice extract will be released. The binder ingredient may be a combination of gums that dissolves in saliva, such as gum Arabic, carrageenan, xanthan gum, konjac gum, agar, or locust bean gum and non-dissolving food fibers. If the binders are xanthan gum, konjac gum, and cellulose fiber, effective dry weight formulations have between 13% and 37% licorice extract, between 33% and 55% food grade gelatin, between 22% and 54% binders, and essentially nothing else but small amounts of concentrated flavoring.

BRIEF DESCRIPTION OF THE DRAWINGS

FIG. 1*a* shows a side view of an oral patch that completely dissolves (erodes).

FIG. 1*b* shows a top view of the same oral patch.

FIG. 2 shows a more conventional non-dissolving oral patch covering a canker sore.

DETAILED DESCRIPTION

FIG. 1 shows an adhesive oral patch that completely dissolves (more precisely, erodes as the molecules become hydrated). In the mouth, it has a feel and texture like hard gummy candies. It is made with slowly dissolving hydrocolloids so that that it typically lasts in the mouth for at least one to six hours. The patch can be formed in the shape of a tablet or a lozenge or a wafer or any other desired shape. The preferred shape is a thin lentil which may be nearly flat on one side as shown in FIG. 1*a*. A detailed description of the patch and how to make it are disclosed by the same inventor in U.S. patent application Ser. No. 10/287,843 filed Nov. 5, 2002 which is incorporated into this document by reference.

To cause the patch to dissolve (erode) very slowly in saliva, a binder that dissolves slowly in saliva is incorporated. Binders that have been tested and found to work well include carrageenan (preferably kappa), xanthan gum combined with konjac gum, and agar. Another useable gum is gum arabic. Other gums similar to those listed, such as locust bean gum which has properties similar to konjac gum, and guar gum should also work.

In addition to causing the patch to erode very slowly in the mouth, the binder also moderates any strong flavors by spreading out over a long period of time the release of that flavor. Consequently, sweeteners and other products to mask strong flavors are not required, although some users prefer a small amount of sweetener and some also prefer the addition of other flavors.

The preferred method of manufacturing the patches of FIG. 1 is to use gum drop manufacturing equipment, squirting a hydrated mixture heated above the gel melting temperature through nozzles onto a cornstarch mold, allowing the patches to cool and gel, drying the patches, and releasing them from the molds. The patches are preferably dried until the water activity level is lower than 0.8 so that the patches will not grow mold or other organisms. The patches are packaged with a hermetic seal to prevent absorption of water moisture from air.

Alternatively, instead of depositing hydrated mixture onto cornstarch molds, the mixture may be deposited as an array of hot, viscous drops onto a sheet of high temperature plastic or coated paper. The drops are allowed to cool and then the sheets of plastic or coated paper with the drops on them are dried in a drying room or oven till the water activity level less than 0.8. The product is sold still adhered to the plastic or paper and the user pulls it off the plastic or paper.

FIG. 2 shows a more conventional non-dissolving oral patch comprising a permeable sponge layer 1 and a non-permeable smooth outer layer 2. The oral patch is covering a canker sore 3 in a human cheek 4. The sponge layer 1 may be fibrous such that small fibers protrude from the surface and engage the mucous lining of the cheek. The fibers may comprise a non-woven mat such as a mat of cotton or synthetic, preferably a hydrophilic synthetic. The outer layer 2 is preferably smooth to minimize dislodging of the patch and may be formed of any flexible thermoplastic. Medication is held in the sponge 1 either by using a high viscosity liquid medication that slowly oozes out of the sponge or by binding the medication to the sponge with slowly dissolving binders such as any of the gums described above, including gelatin. A hot mixture of gums dissolved in water may be massaged into the sponge and then allowed to gel by cooling. A preferred size for the patch is 24 millimeters by 18 millimeters, and one or both layers of the patch may include a red pigment to color it like the inside of the mouth.

Alternatively, any of the other oral patches known in the art may be used.

For medication to be placed in the patch, any of the above-mentioned may be used. Using licorice root extract (*glycyrrhiza* extract) presents significant advantages over pharmaceutical antibiotics because, in the quantities that a person could use per day, no side affects have been discovered. A preferred quantity of licorice extract in each patch that lasts 1 to 6 hours is 20 to 95 milligrams. A person would have to consume more than 10 oral patches to achieve a dose of one gram of extract, which is still a quite moderate dose for treatment of stomach ulcers. Nevertheless, because the licorice extract is concentrated on the canker sore by the patch, the treatment is effective for speeding the healing of the canker sores.

The component of licorice extract that causes side effects is glycyrrhizic acid, a steroid-like component of glycyrrhizic acid, which is the negative part of the salt glycyrrhizin, which is a major ingredient in simple water extract of licorice root. When dissolved in water, the glycyrrhizic acid becomes bio-available from the glycyrrhizin. Aided by the enzyme glucuronidase which is in all body fluids including saliva, this component hydrolyzes to release steroid-like glycyrrhetic acid which causes undesirable side effects when taken in too large a quantity. To avoid these side effects, the simple extract may be modified to reduce the concentration of glycyrrhizin, such as by the well known process for producing deglycyrrhizinated licorice (DGL) described in U.S. Pat. No. 3,046,195 which reduces but does not eliminate the glycyrrhizin. However, in moderate quantities, the anti-inflammatory effect of the glycyrrhetic acid is desirable for reducing pain, so a desirable form of licorice root extract for use in the patches retains the glycyrrhetic acid because the quantities required are far below the side effect threshold. Such a simple extract, denominated spray dried licorice extract, is offered by many suppliers.

The preferred patch formulation is made by combining the licorice extract with collagen and with binder ingredients. Collagen, which is the organic molecule that makes up skin and the lining of the mouth (a form of skin), tends to adhere very well to itself, making it glutinous, and therefore adheres very well to the lining of the mouth. An effective and cost effective form of collagen is food grade gelatin which is made from animal skins. As the collagen molecules slough off the patch while it slowly dissolves (erodes), they tend to adhere to the nearby mouth lining, forming a film. This film significantly reduces the sensitivity of the ulcer, both to touch and to chemical irritants.

If the collagen is bound too tightly by binder ingredients, the patch will not be adherent enough to stay in place. If there is too much collagen, the patch will be too adherent for comfort, especially since the patch is adherent on both sides.

If the entire compound is bound too tightly, it will not erode at a fast enough rate to release the active ingredients on a desired schedule. If the compound is not bound tightly enough, the patch will fall into pieces.

It is preferable to have as much licorice extract as possible for maximum effectiveness. But if there is too much extract, the collagen will not be adherent enough or the binder will not be strong enough or both. This problem is not present if a concentrated active ingredient is used, such as penicillin. So, for licorice root extract, it is best to have very few other ingredients besides the extract, collagen, and binders. Also, many possible ingredients that might be added will reduce the adherence of the collagen, for example, oil, such as mineral oil or peppermint oil or menthol, and glycerin, even in very small quantities, will reduce adhesion.

Testing shows that, if the binders are xanthan gum, konjac gum, and cellulose fiber, effective dry weight formulations have between 13% and 37% licorice extract, between 33% and 55% food grade gelatin, between 22% and 54% binders, and essentially nothing else but perhaps small amounts of concentrated flavoring.

Presented below are conclusions from testing on 49 subjects of the adherent, soluble oral patches with about 31% deglycyrrhizinated licorice (DGL) (about 3% glycyrrhizin):

Pain Relief

Using a licorice extract patch for 10–15 minutes before a meal reduces pain of the canker sore, and, if used up to commencement of a meal, the pain relief lasts through a typical meal. There is no numbing effect on surrounding tissue.

How Many To Use In A Day

The more hours per day the better. Users who report using 2 or fewer patches per day on an established canker sore, each soluble patch lasting 1–4 hours, often report that it does not work. Users who report using 4–9 patches per day on an established canker sore usually report success. When a sore has just begun and has not yet grown, one to four patches will usually do the job.

How Long To Continue Using The Patches

Use can be discontinued use once the user applies DGL and has no stinging sensation and it has been more than 4 hours since DGL was last on the sore. There are reports of people discontinuing use once the sore was no longer painful and the sore then returned. Everyone who continued to use for 24 hours after the sore was no longer painful reported that the sore did not return.

Catching It Early

If the user catches the canker sore early, shorter treatment is required. The sore will often start in a small cut. Some users report that if they apply one patch to a cut for 1–4 hours before there is any sensation of a canker sore, then they will not get a canker sore from the cut. Other times, the sore starts with a feeling that the mucous layer is becoming too thin in a spot before it become painful. Some users report that if they apply one patch to that spot, no canker sore develops. Some users report that if they begin applying the patch when the canker sore is very small and barely painful, only 24 hours of treatment is required, but if they wait until the sore is as large as a tomato seed, then they need 48 hours of treatment before it starts to heal.

Treatment Of The Tongue

For treatment of the tongue, most users stick a patch (which releases extract on both sides) to the closest tooth. This works particularly well at night.

Braces

Users with braces apply the patch to the braces opposite the canker sore so that the patch is touching the canker sore most of the time and is stuck to the teeth and braces. As it softens, the patch settles into the braces. It will completely dissolve out of the braces in 3–9 hours. All this time it supplies licorice extract medication to the sore.

While particular embodiments of the invention have been described above the scope of the invention should not be limited by the above descriptions but rather limited only by the following claims.

The invention claimed is:

1. An adherent patch that, when held in a human mouth, remains in the mouth as a single item that will not spread to be in a plurality of locations in the mouth at one time and wherein said patch slowly erodes, thereby releasing over time an extract of licorice root wherein said patch consists essentially of, by dry weight:
(a) between 13% and 37% extract of licorice root, wherein said extract of licorice root is a water extract;
(b) an adhesive ingredient that adheres to wet surfaces in a human mouth.
(c) between 22% and 54% binder ingredients.

2. The patch of claim 1 where the binder ingredients comprise at least one of: gum arabic, carrageenan, xanthan gum, konjac gum, agar, locust bean gum, and insoluble food fiber.

3. The patch of claim 2 where the binder ingredients include an insoluble food fiber in the form of cellulose fibers.

4. The patch of claim 1 wherein the licorice root extract comprises reduced glycyrrhizin.

5. The patch of claim 1 wherein the licorice root extract comprises glycyrrhizin.

6. The patch of claim 1 wherein the licorice root extract comprises glycyrrhetenic acid.

7. The patch of claim 1 wherein said adhesive ingredient is collagen.

8. The patch of claim 7 wherein the collagen is food grade gelatin.

9. The patch of claim 7, wherein said collagen is present between 33% and 55%.

10. The patch of claim 1 wherein when said patch is exposed to saliva in the human mouth the patch releases said extract of licorice root over more than 30 minutes.

* * * * *